United States Patent [19]

Franklin

[11] Patent Number: 4,929,748

[45] Date of Patent: May 29, 1990

[54] METHOD OF PREPARING DIALKYL DICARBONATES

[75] Inventor: Ralph Franklin, Naperville, Ill.

[73] Assignee: Akzo America Inc., New York, N.Y.

[21] Appl. No.: 281,123

[22] Filed: Dec. 7, 1988

[51] Int. Cl.$^5$ .................. C07C 68/04; C07C 69/96
[52] U.S. Cl. ................................ 558/276; 568/613
[58] Field of Search ........................................ 558/276

[56] References Cited
FOREIGN PATENT DOCUMENTS 46-6895  2/1971  Japan ................................. 558/276

*Primary Examiner*—Vivian Garner
*Attorney, Agent, or Firm*—Louis A. Morris; Jeffrey S. Boone; David H. Vickrey

[57] ABSTRACT

A dialkyl dicarbonate (dialkyl pyrocarbonate) is prepared by contacting an alkyl haloformate (such as ethyl chloroformate) with an alkali metal carbonate (such as potassium carbonate) in the presence of a catalytic amount of a crown ether (such as 18 crown 6) and a solvating amount of a solvent (such as acetonitrile). The process of the invention is easy to carry out, it does not employ particularly hazardous materials, and provides a high yield of dicarbonate.

21 Claims, No Drawings

METHOD OF PREPARING DIALKYL DICARBONATES

BACKGROUND OF THE INVENTION

This invention relates to methods of preparing dialkyl dicarbonates.

Dialkyl dicarbonates, also known as dialkyl pyrocarbonates, are useful as fermentation inhibitors in wines and fruit juices, as well as reagents in chemical syntheses. Several methods are known for preparing dialkyl dicarbonates, but these methods suffer from various disadvantages such as hazardous starting materials (such as phosgene), low yields, and cumbersome purification steps.

One interesting approach is that described in FR 1,483,460 (Shamshurin—Institut Khimii an Moldavskoissr, granted in 1967). The method of the French patent is to react an alkyl chloroformate with potassium or sodium carbonate in the presence of a tertiary amine as a catalyst. While this method is in many respects an improvement over the prior art which proceeded it, it nonetheless is less than an ideal solution. In particular, the purification step necessary to separate the dialkyl dicarbonate from the tertiary amine is rather cumbersome, and the overall process has a disappointingly low yield.

Accordingly, it would be desirable to have a process for preparing dialkyl dicarbonates, which process is safe and convenient to carry out and provides relatively high yields of desired product.

SUMMARY OF THE INVENTION

The instant invention is a process of preparing dialkyl dicarbonates by contacting together an alkyl haloformate and an alkali metal carbonate. This reaction takes place in the presence of a crown ether and a suitable solvent. The process of the invention is particularly easy to carry out, employs less hazardous materials than many prior processes, does not involve cumbersome separation techniques, and results in a relatively high yield.

DETAILED DESCRIPTION OF THE INVENTION

A first component of the invention is an alkyl haloformate according to the formula:

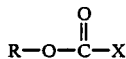

wherein R is an alkyl moiety and X is halogen. R desirably has 1 to 20 carbon atoms, preferable 1 to 10 carbon atoms, and most preferably 2 to 8 carbon atoms. Exemplary alkyl moieties which may be R include ethyl, butyl, 2-ethylhexyl, and allyl. X is desirably fluorine, chlorine, bromine, or iodine, preferably fluorine, chlorine, or bromine, and most preferably chlorine.

The synthesis of these alkyl haloformates is well known to those skilled in the art, and those based upon chlorine are commercially available in large quantities.

Another compound necessary for the practice of the invention is an alkali metal carbonate of the formula:

$M_2CO_3$ wherein M is an alkali metal. M is desirably lithium, sodium or potassium, preferably sodium or potassium, and most preferably potassium. These materials are well known and are commercially available.

The alkyl haloformate and alkali metal carbonate react together in a molar ratio of 2:1. It is therefore desirable that those reactants be present in approximately a 2:1 ratio. However, it can be advantageous to have a slight excess of alkali metal carbonate in order to ensure a reasonably short reaction time. Desirably the alkali metal carbonate is present at 45 to 300, preferably 50 to 100, and more preferably 55 to 60 mole % based on the alkyl haloformate.

A third component of the invention is a catalytic amount of a crown ether. Crown ethers are so named because their cyclic structure resembles a jeweled crown. They are typically named by giving the combined total of carbon and oxygen atoms, the word crown, and the number of oxygen atoms. Thus, 18 crown 6 has the empirical formula $C_{12}H_{24}O_6$ and the structural formula:

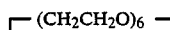

The crown ethers catalyze the reaction, apparently by complexing with the alkali metal of the alkali carbonate, thus allowing the free carbonate moiety to react with the alkyl haloformate. In this regard, it is desirable that the crown ether efficiently complex with the alkali metal to maximize the reaction. Thus, preferred crown ethers are those which complex most efficiently with the particular alkali metal being employed. If sodium or lithium are being used, 15 crown 5 is a particularly preferred crown ether. If potassium is being used, then 18 crown 6 is particularly preferred. Indeed, the combination of potassium and 18 crown 6 is much more efficient than any other metal/crown ether combination evaluated in this invention. As with the other reagents, crown ethers are well known to those skilled in the art and are commercially available.

The crown ether is used in a catalytic amount. By catalytic amount is meant an amount such that the presence of crown ether increases the rate of reaction of the alkyl haloformate and the alkali metal carbonate. While the precise amount of crown ether which constitutes a catalytic amount will vary depending on the particular alkyl haloformate and alkali metal carbonate chosen, in general the crown ether will be present at 0.05 to 10, preferably 0.5 to 5, and most preferably 1 to 1.5 mole percent based on the alkali metal carbonate.

A fourth component of the invention is a solvating amount of a liquid which will solvate the reactants and the complex of the alkali metal and the crown ether. While many compounds will dissolve the reactants, compounds which will also readily dissolve the alkali metal-crown ether complex represents a much smaller class. If it is desired to use a particular solvent, a simple trial will determine if it is suitable. Materials which are operable in the invention include acetonitrile, dichloromethane, toluene, tetrahydrofuran (THF), and N,N-dimethylformamide (DMF). Of these named solvents, acetonitrile, and dichloromethane are preferred, and acetonitrile is particularly preferred because of its extreme efficiency in providing a high yield in a relatively short time.

The reactants may be combined in any convenient matter, but it is preferred that certain procedures be followed in order to maximize the yield. In particular, the presence of water is detrimental to the reaction and the use of anhydrous ingredients and other water exclusion means is therefore recommended. Further, it is preferred that the alkali metal carbonate, the crown ether, and solvent be added to a reaction vessel and stirred while the alkyl haloformate is slowly added. Since the reaction is exothermic, the temperature of the reaction will increase. Higher temperatures will increase the reaction rate, but simultaneously will increase the reaction rate of desired product to undesired dialkyl monocarbonate. The reaction temperature is desirably −30° to 100° C., and preferably 0° to 60° C. The total reaction time is typically ½ to 24 hours, with 1 to 8 hours being preferred.

The invention will be further described in the following examples:

EXAMPLE 1

A 1 liter, 3-necked flask was equipped with a reflux condenser, dropping funnel, thermometer, mechanical stirrer and calcium chloride drying tubes. The flask was charged with 70 g (0.51 mole) of powdered, anhydrous potassium carbonate; 2 g (0.0076 mole) 18-crown-6 ether and 250 ml of acetonitrile. The reaction mixture was efficiently stirred while 122.5 g (1 mole) of isopropyl chloroformate was added dropwise at such a rate as to maintain a reaction temperature of not more than 40° C. The reaction mixture was stirred for a total of 6 hours and then allowed to stand overnight prior to work up.

The reaction mixture was worked-up by filtering off the inorganic salts and removing the solvent on a rotary evaporator at 30° C. using a water aspirator to provide the vacuum. The resulting liquid was dissolved in 200-300 ml of dichloromethane and washed twice with 100 ml portions of water. After drying over magnesium sulphate, filtering, and stripping of solvent, 80.7 g of a clear liquid was obtained. Analysis by Carbon-13 NMR showed the crude product to consist of almost entirely di-isopropyl dicarbonate. Careful vacuum distillation of the crude product gave 77.4 g (0.41 mol) of pure di-isopropyl dicarbonate (boiling point 44°–48° C. at 0.25 mm Hg; overall yield 82%).

EXAMPLE 2

A 250 ml, 3-necked flask was equipped with a dropping funnel, thermometer, reflux condenser, calcium chloride drying tubes and a magnetic stirring bar. 7.7 g (0.056 mole) of powdered anhydrous potassium carbonate, 0.2 g (0.00076 mole) of 18-crown-6 ether, and 25 ml of acetonitrile were charged into the flask. 1 g diethylene glycol diethyl ether was then added as an internal standard for GLC analysis. The reaction mixture was stirred and 12.2 g (0.1 mole) isopropyl chloroformate was added dropwise over 1 hour while maintaining a reaction temperature of no more than 40° C. GLC analysis after 110 minutes showed 2.5% of chloroformate remaining; analysis after 190 minutes showed all of the chloroformate to have been consumed. The reaction was worked up in a fashion similar to Example 1. The resulting product (8.6 g, 90% crude yield) was found to consist of 12% Diethylene glycol diethyl ether and 88% di-isopropyl dicarbonate; this gives an overall yield of dicarbonate of 80%.

EXAMPLE 3

Using the same apparatus as described in Example 2; 13.6 g (0.1 mole) of n-butyl chloroformate was added dropwise over 1 hour to a stirred mixture of 7.7 g (0.056 mole) powdered, anhydrous potassium carbonate and 1.0 g diethylene glycol diethyl ether (internal GLC standard) in 25 ml of acetonitrile. GLC analysis 1 hour after completion of the chloroformate addition showed very little reaction having occurred. At this point 0.2 g (0.00076 mole) of 18-crown-6 ether was added to the reaction mixture. An immediate exotherm occurred raising the temperature from 25° to 47° C.; GLC analysis 1 hour later showed no chloroformate remaining. Infra-red spectroscopy of the reaction solution confirmed the formation of di(n-butyl) dicarbonate.

EXAMPLE 4

Following the procedure of Example 2, isopropyl chloroformate was reacted with anhydrous potassium carbonate and 18-crown-6 crown ether in a variety of solvents. The reaction was monitored by GLC using an internal standard method and the results are illustrated below:

| Catalyst | Reaction Time (Minutes) | % Reacted Chloroformate | % Conversion to Dicarbonate | % Yield |
|---|---|---|---|---|
| Acetonitrile | 120 | 96 | 89 | 85 |
| Dichloromethane | 120 | 72 | 87 | 63 |
| Toluene | 120 | 63 | 72 | 45 |
| Tetrahydrofuran | 120 | 63 | 72 | 45 |
| Dimethylformamide | 120 | 99 | 55 | 54 |

EXAMPLE 5

Following the procedure of Example 2; various catalysts were evaluated for the preparation of di-isopropyl dicarbonate. The reaction was monitored by GLC (internal standard method) and the results are shown below:

| Catalyst | Reaction Time (Minutes) | % Reacted Chloroformate | % Conversion to Dicarbonate | % Yield |
|---|---|---|---|---|
| 18 Crown 6 | 180 | 100 | 87 | 87 |
| Aliquat 336 | 180 | 51 | 91 | 46 |
| Arquad 2C/75 | 180 | 47 | 92 | 43 |
| Tetrabutylammonium hydrogen sulphate | 180 | 35 | 93 | 32 |
| Triethylamine | 180 | 32 | 78 | 25 |

EXAMPLE 6

Following the procedure of Example 2, metal carbonate salts other than potassium carbonate were evaluated for the preparation of di-isopropyl dicarbonate. The GLC analysis of the reaction mixture is shown below:

| Metal Carbonate | % Reaction Time | % Reacted Chloroformate |
|---|---|---|
| Sodium Carbonate | 180 | 10 |
| Lithium Carbonate | 180 | 1 |

EXAMPLE 7

Several chloroformates were reacted with potassium carbonate using the same basic method as described in Example 2. The reactions were run for a total time of 3 hours and then worked-up. The isolated crude product was analyzed by Carbon-13 NMR, the yield and product distribution data is shown in the table below:

| Chloroformate | Overall Yield % | Composition Dicarbonate | Monocarbonate | Dicarbonate % Yield |
|---|---|---|---|---|
| Ethyl | 74 | 85 | 15 | 63 |
| Butyl | 86 | 70 | 27 | 60 |
| 2-Ethylhexyl | 96 | 80 | 18 | 77 |
| Allyl | — | — | 100 | 0 |
| Benzyl | 98 | — | 100 | 0 |

EXAMPLE 8

In a manner similar to Example 7, allyl chloroformate was again reacted with potassium carbonate but their reaction was carried out at 10° C. for 1.25 hours, and the product was then immediately worked up. This procedure gave an 80% overall yield comprising 97% dicarbonate and 3% monocarbonate. The dicarbonate % yield was 78%.

EXAMPLE 9

Iso-propyl chloroformate (6.10 g, 0.05 mole) was added dropwise to a stirred mixture of powdered, anhydrous, sodium carbonate (3.81 g, 0.036 mole) and 4,7,13,16,21-Pentaoxa-1, 10-diazabicycol[8.85]tricosane (0.10 g, 0.00031 mole) in acetonitrile (12 ml) at such a rate as to maintain a reaction temperature of 40° C. The reaction mixture was stirred for a total of 11 hours and allowed to stand overnight prior to work-up. The product was isolated in a similar fashion to Example 1. After vacuum distillation a 71% yield of di-isopropyl dicarbonate was obtained.

EXAMPLE 10

In a manner similar to Example 9, Kryptofix 222 (4,7,13,16,21,24-Hexaoxa-1,10-diazabicyclo[8.8.8]hexacosane) was used as the catalyst at 0.76 mole% relative to sodium carbonate. The yield of distilled product was 56%.

Repeating the reaction with Kryptofix 222 using diethyl ether as the solvent, a 42% yield of distilled product was obtained after stirring for 7½ hours and standing overnight.

I claim:

1. A method for preparing a dialkyl dicarbonate comprising contacting together:
   (a) an alkyl haloformate wherein the alkyl group contains 1 to 20 carbon atoms; and
   (b) an alkali metal carbonate; in the presence of
   (c) a catalytic amount of a crown ether; and
   (d) a solvating amount of a liquid which will dissolve a complex of the alkali metal and the crown ether.

2. The method of claim 1 wherein the halo atom of the alkyl haloformate is fluorine, chlorine or bromine.

3. The method of claim 2 wherein the halo atom of the alkyl haloformate is chlorine.

4. The method of claim 1 wherein the alkyl group contains 1 to 10 carbon atoms.

5. The method of claim 1 wherein the solvent is acetonitrile, dichloromethane, toluene, tetrahydrofuran, or dimethylformamide.

6. The method of claim 5 wherein the soluent is acetonitrile.

7. The method of claim 1 wherein the alkali metal carbonate is a carbonate of lithium, sodium, or potassium.

8. The method of claim 7 wherein the alkali metal carbonate is a carbonate of potassium or sodium.

9. The method of claim 8 wherein the alkali metal carbonate is a carbonate of potassium.

10. The method of claim 1 wherein the alkali metal carbonate is present at 45 to 300 mole % based on the alkyl haloformate.

11. The method of claim 10 wherein the alkali metal carbonate is present at 50 to 100 mole % based on the alkyl haloformate.

12. The method of claim 11 wherein the alkali metal carbonate is present at 55 to 60 mole % based on the alkyl haloformate.

13. The method of claim 1 wherein the crown ether is 18 crown 6 or 15 crown 5.

14. The method of claim 13 wherein the crown ether is 18 crown 6.

15. The method of claim 13 wherein the crown ether is present at 0.5 to 5 mole % based on the alkyl haloformate.

16. The method of claim 15 wherein the crown ether is present at 1 to 1.5 mole % based on the alkyl haloformate.

17. The method of claim 1 wherein the crown ether is present at 0.05 to 10 mole % based on the alkyl haloformate.

18. The method of claim 1 wherein the reaction takes place at −30° to 100° C.

19. The method of claim 18 wherein the reaction takes place at 0° to 60° C.

20. The method of claim 1 wherein the reaction takes place within 0.5 to 24 hours.

21. The method of claim 20 wherein the reaction takes place within 1 to 8 hours.

* * * * *